United States Patent [19]

Wang et al.

[11] Patent Number: 5,646,186

[45] Date of Patent: Jul. 8, 1997

[54] RETINOID COMPOSITION

[75] Inventors: Jonas C. T. Wang, Robbinsville, N.J.; Stephen J. Wisniewski, Doylestown, Pa.

[73] Assignee: Johnson & Johnson Consumer Products, Inc., Skillman, N.J.

[21] Appl. No.: 241,446

[22] Filed: May 17, 1994

[51] Int. Cl.$^6$ .......................... A61K 31/19; A61K 31/07
[52] U.S. Cl. .......................... 514/557; 514/725; 514/844; 514/922; 514/974
[58] Field of Search ........................... 514/557, 725, 514/844, 922, 974

[56] References Cited

U.S. PATENT DOCUMENTS

| | | | |
|---|---|---|---|
| 4,234,599 | 11/1980 | Van Scott et al. | 424/279 |
| 4,294,852 | 10/1981 | Wildnauer et al. | 424/317 |
| 4,877,805 | 10/1989 | Kligman | 514/381 |
| 5,093,360 | 3/1992 | Yu et al. | 514/463 |
| 5,153,230 | 10/1992 | Jaffery | 514/847 |

FOREIGN PATENT DOCUMENTS

| | | | |
|---|---|---|---|
| 0413528A1 | 8/1990 | European Pat. Off. | A61K 7/48 |
| 0566405A2 | 4/1993 | European Pat. Off. | A61K 9/06 |

OTHER PUBLICATIONS

Article by Lisa Kintish "New Ingredients and Formulatoins are Croppling up in cosmeceuticals and Treatment Products for the Skin; 694 Soap, Cosmetics, chemical Specialities" 69 (1993) Feb. No. 2, New York, US.
Remingtons Pharmaceutical Sciences, 18th ed., 1990, pp. 1504–1507.

*Primary Examiner*—Kimberly Jordan

[57] ABSTRACT

This invention relates to skin care compositions containing retinoids which are generally applied topically to improve the quality of the skin. More particularly, this invention relates to skin care compositions comprising retinol (Vitamin A alcohol) and further comprising irritation ameliorating quantities of glycolic acid.

11 Claims, 3 Drawing Sheets

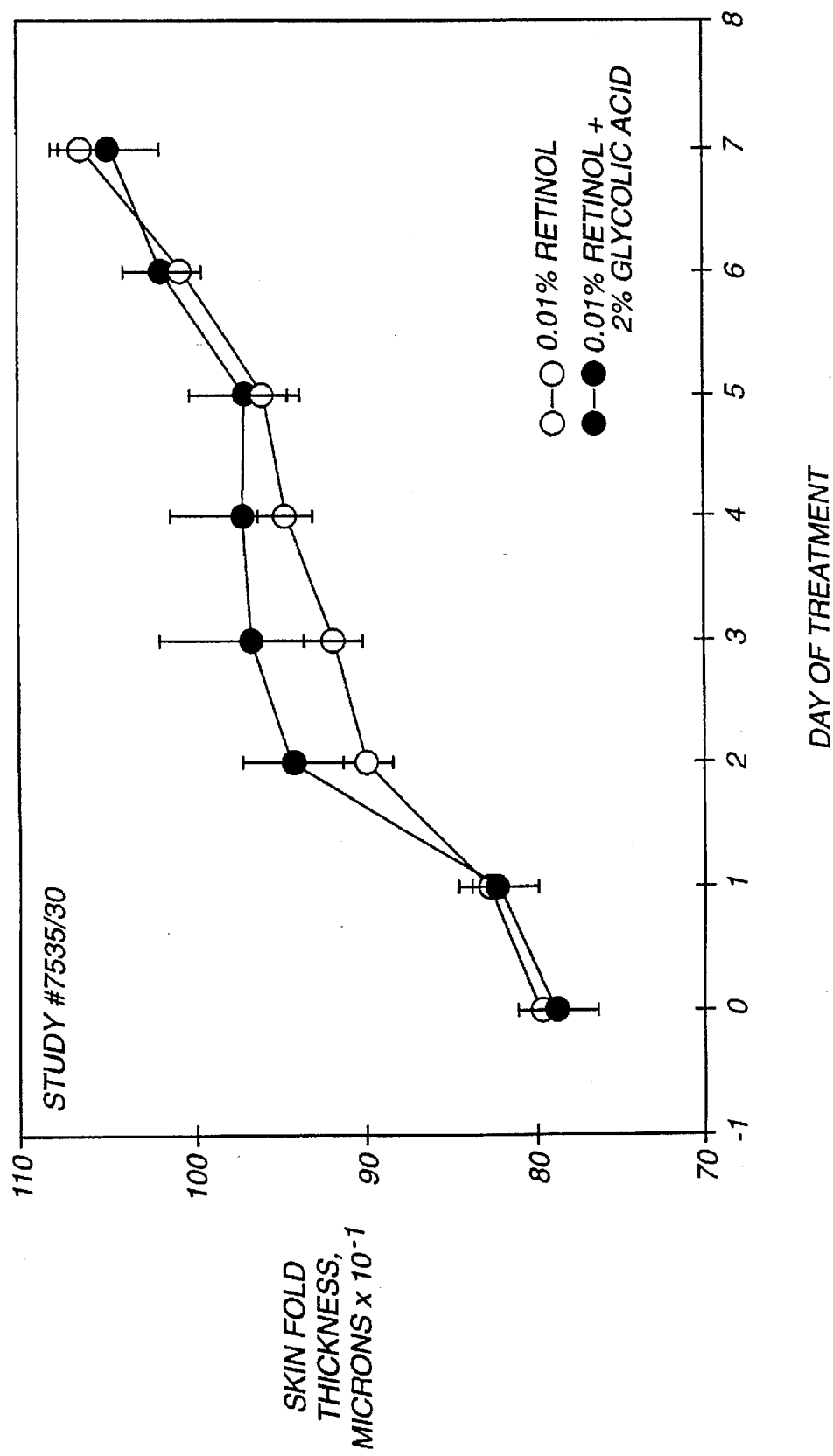

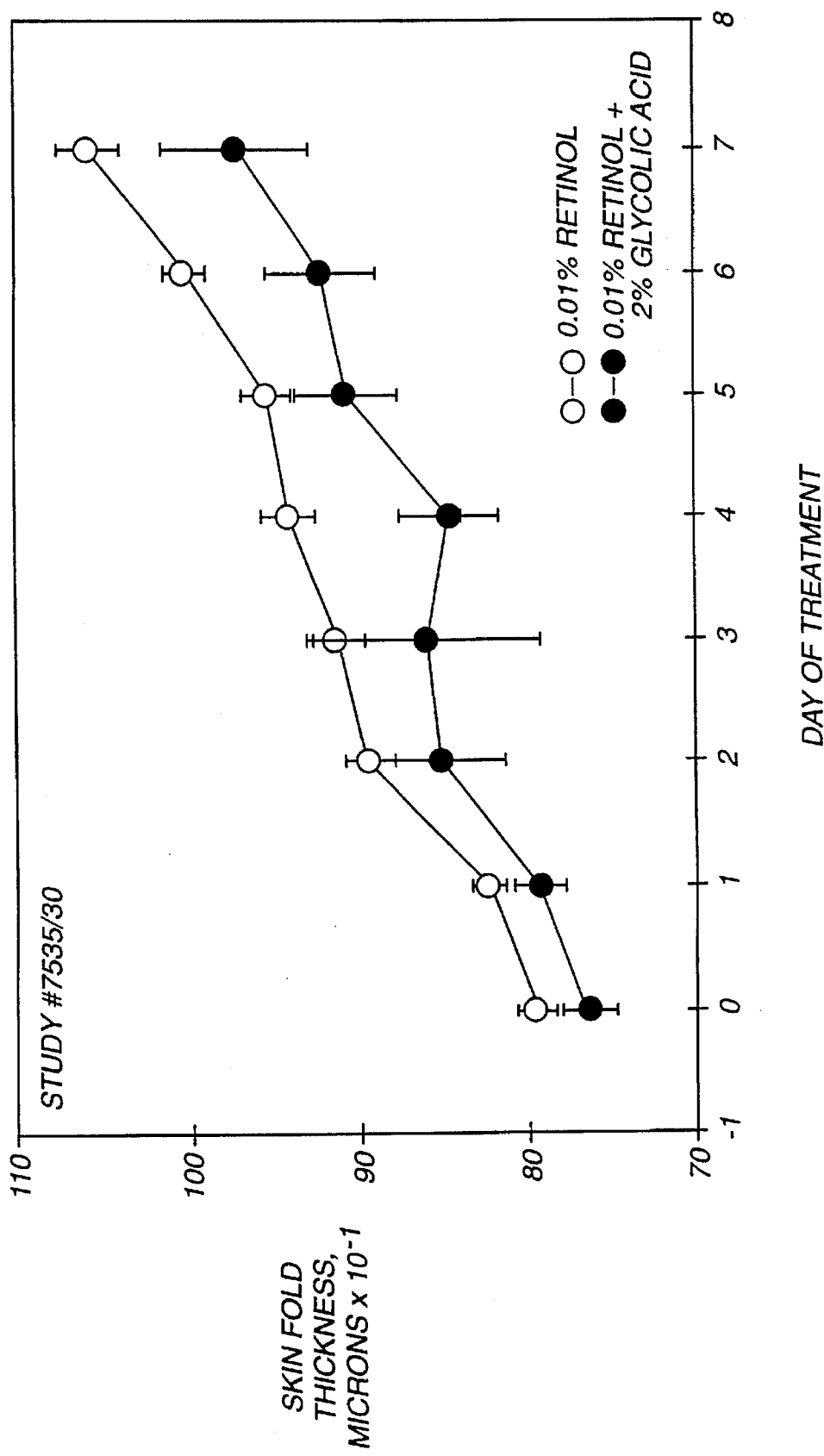

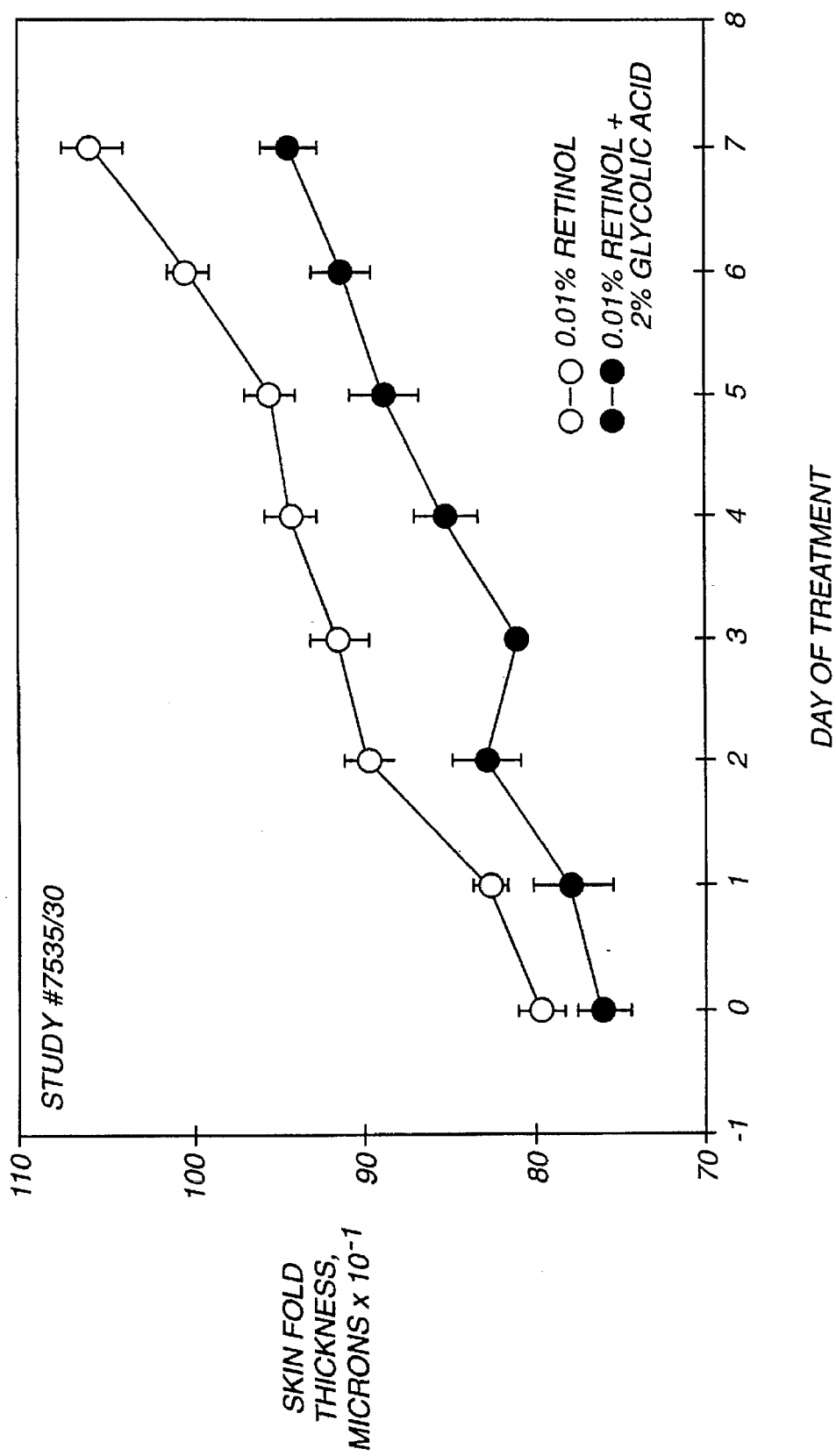

5,646,186

RETINOID COMPOSITION

FIELD OF THE INVENTION

This invention relates to skin care compositions containing retinoids which are generally applied topically to improve the quality of the skin. More particularly, this invention relates to skin care compositions comprising retinol (Vitamin A alcohol) and further comprising irritation ameliorating quantities of glycolic acid.

BACKGROUND OF THE INVENTION

Skin care compositions containing retinoids have become the focus of great interest in recent years. Retinoic acid, also known as Vitamin A acid or tretinoin, is well-known for the treatment of such skin conditions as acne and products containing retinoic acid are commercially available in various forms from the Dermatological Division of Ortho Pharmaceutical Corporation.

More recently, however, wider use of retinoids has been suggested for treatments other than ache such as, for example, the treatment of skin against photoaging and sun damage. Many individuals who have had a good deal of sun exposure in childhood will show the following gross cutaneous alterations in later adult life: wrinkling, leatheriness, yellowing, looseness, roughness, dryness, mottling (hyperpigmentation) and various premalignant growths (often subclinical). These changes are most prominent in light-skinned person who burn easily and tan poorly. These cumulative effects of sunlight are often referred to as "photoaging". Although the anatomical degradation of the skin is most advanced in the elderly, the destructive effects of excessive sun exposure are already evident by the second decade. Serious microscopic alterations of the epidermis and dermis occur decades before these become clinically visible. Wrinkling, yellowing, leatheriness and loss of elasticity are very late changes.

The problem of skin aging is addressed in U.S. Pat. No. 4,603,146 wherein Vitamin A acid in an emollient vehicle is suggested as a treatment. Further, in U.S. Pat. No. 4,877,805, it is suggested that a number of retinoids are useful for restoring and reversing sun damage of human skin.

When considering the use of retinoids in skin care products, it is believed that certain retinoids such as, for example, retinol (Vitamin A alcohol), would be preferred over retinoic acid. This is because retinol is an endogenous compound naturally occurring in the human body and essential for good growth, differentiation of epithelial tissues and reproduction. Retinol is also preferred because it has a much larger safety margin than other retinoids such as retinoic acid. Accordingly, attention has turned toward formulating skin care compositions which contain retinol. Such compositions have been proposed such as those disclosed in a pending patent application, U.S. Ser. No. 719,264, filed on Jun. 27, 1991 by Clum et al. and commonly assigned to the assignee of this application; the disclosure of which is hereby incorporated by reference.

The benefits from the use of retinol as set out above notwithstanding, it has been noted that skin care compositions containing retinol to some degree exhibit undesirable skin irritation as manifested by flaking, erythema and dermal edema.

Accordingly, there is a need for a composition comprising retinol which manifests less retinol induced irritation.

SUMMARY OF THE INVENTION

In accordance with the teachings of this invention, a skin care composition is provided comprising retinol as an active ingredient. The retinol irritating properties of the composition are ameliorated by employing a retinol irritation ameliorating amount of glycolic acid.

The glycolic acid is present in an amount effective to ameliorating such indicia of retinol skin irritation as transepidermal water loss (hereinafter "TEWL") and skin fold thickness (hereinafter "SFT"). TEWL measures a change in barrier function (i.e. the thinning of the stratum corneum results in increased TEWL) and SFT in an indication of dermal edema. Both a decrease in barrier function and an increase in dermal edema are characteristic indications of irritation resulting from the topical application of retinol. Such effective amounts of glycolic acid are preferably greater than about two percent by weight of the composition and still more preferably from about five to about ten percent by weight glycolic acid, based on the weight of the composition.

BRIEF DESCRIPTION OF THE DRAWINGS

FIG. 1 is a graphical representation of data illustrating the SFT effect of retinol containing compositions comprising 0% and 2% glycolic acid;

FIG. 2 is a graphical representation of data illustrating the SFT effect of retinol containing compositions comprising 0% and 5% glycolic acid; and FIG. 3 is a graphical representation of data illustrating the SFT effect of retinol containing compositions comprising 0% and 10% glycolic acid.

DETAILED DESCRIPTION OF THE INVENTION

As described above, the composition of this invention comprises retinol and glycolic acid as a retinol irritation ameliorator. As described in the aforementioned application, U.S. Ser. No. 719,264, the retinol composition comprises a therapeutically effective amount of retinol in a vehicle for topical application. Preferably, the vehicle is chosen, in accordance with the teaching of the referred to prior filed application, to include a system for insuring long shelf life and stability for the retinoid.

Accordingly, the retinol concentration in the composition may range from about 0.001 to about 5.0%, by weight of the total composition, and preferably from about 0.001 to about 1.0%. The composition is preferably chosen as water-in-oil emulsion, as such has been found to be particularly protective of the stability of the retinol activity. The ratio of the oil phase to the water phase can vary from about 5:95 to about 99:1, by weight. Additionally, the composition preferably comprises a chemical stabilizing system selected from the group consisting of:

a) a chelating agent and at least one oil-soluble antioxidant;

b) a chelating agent and at least one water-soluble antioxidant; and c) antioxidant present in each of the oil and water phases of said emulsion;

The water-soluble antioxidants which are useful in the compositions of the present invention include ascorbic acid, sodium sulfite, sodium metabisulfite, sodium bisulfite, sodium thiosulfite, sodium formaldehyde sulfoxylate, isoascorbic acid, thioglycerol, thiosorbitol, thiourea, thioglycolic acid, cysteine hydrochloride, 1,4-diazobicyclo-(2,2,2)-octane and mixtures thereof as well as any other known water-soluble antioxidant compatible with the other components of the compositions.

The oil-soluble antioxidants which are useful in the compositions of the present invention include butylated hydroxytoluene (BHT), ascorbyl palmitate, butylated hydroxyanisole (BHA), α-tocopherol, phenyl-α-naphthylamine, hydroquinone, propyl gallate, nordihydroguiaretic acid, and mixtures thereof as well as any other known oil-soluble antioxidant compatible with the other components of the compositions.

The antioxidants would be utilized in a stabilizing effective amount and may range in total from about 0.001 to 5.0% based on the weight of the total composition, preferably from about 0.01 to 1.0%. The amount of antioxidants utilized in the compositions of the present invention is dependent in part on the specific antioxidants selected, the amount of and specific retinoid being protected and the processing conditions.

In certain aspects of this invention, the compositions include a chelating agent. The retinol compound of this invention is sensitive to metal ions and in particular to bi- and tri-valent cations and in certain instances, degrade rapidly in their presence. The chelating agent forms a complex with the metal ions thereby inactivating them and preventing them from affecting the retinol compound. Chelating agents which are useful in the compositions of the present invention include ethylenediamine tetraacetic acid (EDTA) and derivatives and salts thereof, dihydroxyethyl glycine, citric acid, tartaric acid, and mixtures thereof. The chelating agents should be utilized in a stabilizing effective amount and may range from about 0.01 to 2.0% based on the weight of the total composition, preferably from about 0.05 to 1.0%.

The skin care compositions of the present invention comprising a water-in-oil emulsion can be in the format of cream or lotion formulations, as desired, by varying the relative quantities of the oil and water phases of the emulsion. The pH of the compositions should be in the range of from about 4 to about 9, and preferably from about 4 to about 7.

Mineral oils, animal oils, vegetable oils and silicones have all been used in cosmetic creams and lotions of the emulsion type. In addition to such oils, other emollients and surface active agents have been incorporated in the emulsions, including glyceryl trioleate, acetylated sucrose distearate, sorbitan tiolate, polyoxyethylene (1) monostearate, glycerol monoleate, sucrose distearate, polyethylene glycol (50) monostearate, octylphonoxypoly (ethyleneoxy) ethanol, decaglycerin penta-isostearate, sorbitan sesquioleate, hydroxylated lanolin, lanolin, triglyceryl diisotearate, polyoxyethylene (2) oleyl ether, calcium stearoyl-2-lactylate, methyl glucoside sesquistearate, sorbitan monopalmitate, methoxy polyethylene glycol-22/dodceyl glycol copolymer (Elfacos E200), polyethylene glycol-45/dodecyl glycol copolymer(Elfacos ST9), polyethylene glycol 400 distearate, and lanolin derived sterol extracts, glycol stearate and glyceryl stearate; alcohols, such as cetyl alcohol and lanolin alcohol; myristates, such as isopropyl myristate; cetyl palmitate; cholesterol; stearic acid; propylene glycol; glycerine, sorbitol and the like. Thickeners such as natural gums and synthetic polymers, as well as preservatives such as methylparaben, butyl paraben, propylparaben and phenoxyethanol, coloring agents and fragrances also are commonly included in such compositions. Other active ingredients such as sunscreen materials and antimicrobial materials may be utilized in the compositions of the present invention provided that they are physically and chemically compatible with the other components of the compositions.

In accordance with this invention, the above described retinol composition further comprises glycolic acid as a retinol irritation ameliorating component. Glycolic acid (2-hydroxyethanoic acid) is one of the class of alpha hydroxyacids of which for example, lactic acid (2-hydroxy propanoic), malic acid (2-hydroxybutane-1,4,dioic acid) are also close members. It is naturally occurring, as are other alpha hydroxyacids obtained from fruits, sugar cane, and yogurt and its effects on skin and skin disfunctions have been already studied. (See, for example E. J. Van Scott and R. J. Yu, Control of keratinization with alpha hydroxy acids and related compounds, Arch Dermatol 110 586–590 (1974); E. J. Van Scott and R. J. Yu, Commentary: Ichthyosis and keratinization, Arch Dermatol 118 860–861 (1982); E. J. Van Scott and R. J. Yu, Hyperkerarinization, corneocyte cohesion, and alpha hydroxy acids, J Am Acad Dermatol 11 867–879 (1984); E. J. Van Scott, Dry skin et cetera, corneocyte detachment, desquamation, and neo strat, Int J Dermatol 26 90 (1987); E. J. Van Scott, Alpha hydroxy acids effective for acne, warts, dry skin, Skin & Allergy News 18 35 (1987); E. J. Van Scott and R. J. Yu, Alpha hydroxy acids: Procedures for use in clinical practice, Cutis 43 222–228 (1989).

Further, in European Patent Application 87117405.8 published Jul. 6, 1988, Scott and Yu disclosed employing an alpha hydroxy acid salt, ethyl pyruvate, with retinoic acid as a treatment for oily skin. In U.S. Pat. No. 5,153,230 to Monzour H. Jeffrey, it is suggested that glycolic acid is in itself useful for treating aging skin and may be combined with Vitamin A palmitate in such composition.

In view of these references, however, it is totally surprising that glycolic acid may be employed in a retinol containing composition to ameliorate the irritating effects of the retinol component. For example, Scott and Yu in Arch Dermatol/Vol. 110, October 1974, p588 have stated that glycolic acid, particularly in concentrations of from 5 to 10%, when used as the sole active ingredient, has acted as an irritant and hence, lower concentrations are recommended. Additionally, the authors further noted that one effect of glycolic acid is an abrupt loss of the entire abnormal stratum corneum in patients with lamellar ichthyosis. Accordingly, it is entirely surprising that glycolic acid, when combined with a specific irritating retinoid, retinol, can have an irritation ameliorating effect on the combination.

To illustrate the invention and the advantages flowing therefrom, the following examples are given. In each of these examples, the retinol containing compositions are emulsions prepared in accordance with the following procedure:

The ingredients shown under the heading "Aqueous Phase ingredients" in the table below are combined and heated until dissolved at a temperature of 55° to 60° C. and then cooled to 55° C. or until clear and then adjusted to a pH of 4.7 using a 50% by weight sodium hydroxide solution. The pH adjusted Aqueous Phase is then heated to 75° C. The ingredients shown under the heading "Oil Phase Ingredients" are combined and heated to 75° C. The Aqueous Phase is then added to the oil phase and heating is terminated. When the mixture reaches a temperature of 45° to 50° C. the fragrance is added and additionally, the ionized water is added to weight. The mixture is then homogenized for one minute. The retinol mixture is then added with stirring and the combined mixture is allowed to cool with stirring to room temperature.

| COMPOSITION: For 500 g | 1 CONTROL | 2 VEHICLE | 3 0.01 RETINOL 0.0 GLYCOLIC ACID | 4 0.01 RETINOL 2% GLYCOLIC ACID | 5 0.01 RETINOL 5% GLYCOLIC ACID | 6 0.01 RETINOL 10% GLYCOLIC ACID |
|---|---|---|---|---|---|---|
| Aqueous Phase Ingredients | | | | | | |
| Deionized Water | 0 | 266.75 | 266.75 | 256.75 | 241.75 | 216.75 |
| Sorbitol | 0 | 25.0 | 25.0 | 25.0 | 25.0 | 25.0 |
| Dehydroacetic Acid | 0 | 1.25 | 1.25 | 1.25 | 1.25 | 1.25 |
| EDTA | 0 | 0.5 | 0.5 | 0.5 | 0.5 | 0.5 |
| Glycolic Acid | 0 | 0.0 | 0.0 | 10.0 | 25.0 | 50.0 |
| Ascorbic Acid | 0 | 0.5 | 0.5 | 0.5 | 0.5 | 0.5 |
| Oil Phase Ingredients | | | | | | |
| Mineral Oil | 0 | 125.0 | 125.0 | 125.0 | 125.0 | 125.0 |
| [1]Elfacos C-26 | 0 | 30.0 | 30.0 | 30.0 | 30.0 | 30.0 |
| [2]Elfacos E-200 | 0 | 25.0 | 25.0 | 25.0 | 25.0 | 25.0 |
| [3]Elfacos ST-9 | 0 | 15.0 | 15.0 | 15.0 | 15.0 | 15.0 |
| [4]Dow Corning 580 Wax | 0 | 5.0 | 5.0 | 5.0 | 5.0 | 5.0 |
| [5]Dimethicone | 0 | 5.0 | 5.0 | 5.0 | 5.0 | 5.0 |
| [6]BHT | 0 | 0.25 | 0.25 | 0.25 | 0.25 | 0.25 |
| [7]Chemoderm 6401/B | 0 | 0.75 | 0.75 | 0.75 | 0.75 | 0.75 |
| Retinol Mixture | 0 | 0.115 | 0.115 | 0.115 | 0.115 | 0.115 |
| BHA | 0 | 0.0011 | 0.0011 | 0.0011 | 0.0011 | 0.0011 |
| BHT | 0 | 0.0039 | 0.0039 | 0.0039 | 0.0039 | 0.0039 |
| Retinol | 0 | 0.0506 | 0.0506 | 0.0506 | 0.0506 | 0.0506 |
| Tween 20 | 0 | 0.0594 | 0.0594 | 0.0594 | 0.0594 | 0.0594 |

[1]Elfacos C-26 = Hydroxyoctacosanyl Hydroxystearate
[2]Elfacos E-200 = Methoxy PEG-22/Dodecyl Glycol Copolymer
[3]Elfacos ST-9 = PEG-45/Dodecyl Glycol Copolymer
[4]Dow Corning 580 Wax = Stearoxytrimethylsilane
[5]Dimethicone = Dimethicone $(C_2H_6OSi) \times C_4H_{12}Si$
[6]BHT = Butylated Hydroxytoluene
[7]Chemoderm 6401/B = Fragrance Each of the compositions are tested for Transepidermal Water Loss (TEWL) and Skin Fold Thickness (SFT) as markers for retinol irritation. This is accomplished by treating male hairless mice (Skh/hr1, Charles River, Wilmington, Mass.), 6–8 weeks of age. The mice upon receipt were fed ad libitum on Purina Chow #5015 and watered ad libitum for one week prior to use. The mice were then randomly assigned to treatment groups of seven mice each. Each group (with the exception of the control) was treated daily for seven days with one of the compositions set forth below applying 0.1 ml of such composition over the entire dorsal trunk and spreading it by gentle inunction. The study animals remained on a twelve hour light/twelve hour dark cycle before, during and after dosing. TEWL and SFT measurements were taken from each animal just prior to daily retreatment. Care was taken that subsequent TEWL and SFT readings were made as close to twenty-four hour intervals after the treatment as possible to reduce sampling error.

The skinfold thickness test (SFT) was carried out as follows. A fold of dorsal skin parallel to the long axis of each animal was picked up with the fingers. A Mitutuyo Pocket Thickness gauge (cat. #7309, MRO Industrial Supply, Manville, N.J.) was held open, slipped over the fold of skin at a site on the lower midback. The spring-loaded arm of the gauge was released and the gauge slid slightly forward to ensure that no more than 2 thicknesses of skin were picked up. A single reading×0.01 mm at the same site was made for each mouse at each interim. When the skin was edematous and the pressure of the spring caused the gauge reading to slowly decline, the reading was taken after the gauge stopped.

The transepidermal water loss (TEWL) measurements were performed as follows. The evaporimeter employed is an instrument for the quantitative determination of water evaporation, i.e. water transport by diffusion, from or to surfaces in contact with the atmosphere. Mice were held gently and the left flank area held up to the probe of an EP-1 ServoMed Evaporimeter (ServoMed, Stockholm, Sweden), so that an airtight seal was formed. A standard deviation setting of 0.1 was used, and one reading was taken per mouse. The TEWL in $g/m^2/h$ was recorded at each time point.

The result of the TEWL testing is summarized in the following table.

Effect of Glycolic Acid and Retinol on TEWL in Groups of Seven Mice

TEWL - MEAN VALUES ONLY

| | | PRODUCT | | | | |
|---|---|---|---|---|---|---|
| DAY | Untreated Control | .00% + 0% (vehicle) | .01% + 0% glycolic | .01% + 2% glycolic | .01% + 5% glycolic | .01% + 10% glycolic |
| 0 | 7.5 | 7.9 | 7.7 | 7.7 | 8.1 | 8.4 |
| 1 | 9.1 | 10.1 | 11.8 | 12.1 | 12.4 | 14.1 |

Effect of Glycolic Acid and Retinol on TEWL in Groups of Seven Mice

TEWL - MEAN VALUES ONLY

| DAY | Untreated Control | .00% + 0% (vehicle) | .01% + 0% glycolic | .01% + 2% glycolic | .01% + 5% glycolic | .01% + 10% glycolic |
|---|---|---|---|---|---|---|
| 2 | 7.9 | 14.7 | 19.6 | 29.5 | 21.5 | 15.5 |
| 3 | 8.7 | 16.8 | 29.1 | 37.4 | 23.6 | 21.1 |
| 4 | 7.4 | 12.3 | 24.0 | 29.2 | 17.2 | 18.5 |
| 5 | 7.9 | 12.5 | 18.3 | 26.8 | 16.8 | 22.0 |
| 6 | 8.5 | 17.8 | 22.5 | 36.6 | 22.3 | 18.7 |
| 7 | 8.7 | 19.4 | 26.1 | 30.2 | 22.2 | 21.0 |

As can be seen in the above table, the TEWL for the group tested with composition 2, the vehicle, showed irritation based on the increase TEWL and this effect was aggravated substantially when a group was treated with the retinol containing, glycolic acid free, composition 3. A concentration of glycolic acid of as high as 2% by weight (composition 4) further aggravated the irritation. On the other hand, both a 5% glycolic acid composition (composition 5) and a 10% glycolic composition (composition 6) all tended toward ameliorating this irritation.

The results of the skin fold thickness measurements (SFT) are depicted in FIGS. 1-3. As can be clearly seen from the figures, a 2% glycolic acid addition did little to ameliorate the irritation as manifested by SFT in a 0.01% retinol composition (FIG. 1). On the other hand, a 5% glycolic acid addition and still more, a 10% glycolic acid addition, significantly ameliorated such irritation (FIGS. 2 and 3).

Each of the compositions set forth in Table III below was tested for cumulative irritation on human skin. Twenty-five human subjects were screened to ensure that they were in good health and that they did not have allergies or sensitivities to cosmetic products, toiletries and/or topical drugs. They were further questioned to ensure that they did not have any pre-existing or dormant dermatologic conditions, were not on chronic medication, were not pregnant or nursing, participating in other clinical studies or were abusers of alcohol or drugs. The subjects did not receive any experimental drugs within 30 days prior to admission into the study.

The compositions were applied in the following manner. Between about 0.2 and 0.3 ml of the test liquid composition was applied to an occlusive clinical patch. A patch loaded with composition was applied to the left or right upper back area. The patches were applied to the left or right scapular area starting from the top to the bottom of the back and lateral to the midline. The position of the patches was marked with gentian violet.

Each test product was applied under an occlusive patch to the designated test site three times per week (Mondays, Wednesdays and Fridays) for a total of six applications over a fourteen-day period. The patches remained in place for 48 hours during the week (Monday and Wednesday applications) and for 72 hours during the weekend (Friday applications)- After each 48-hour or 72-hour occlusive period, the patches were removed and the test sites graded according to the following scale:

0—No visible reaction
0.5—Minimal erythema
1—Mild erythema
2—Intense erythema
3—Intense erythema+induration+vesicular erosion
4—Intense erythema+induration+bullae Each site was cleansed with sterile saline after which fresh test material and patches were applied to each test site. If grade 3 or 4 irritation was observed on any test site, no further applications were made to the site and the maximum score (4) was assigned for the duration of the study. The six daily scores for each test site for each subject was summed to yield a total score for 14 days. A grand total for a test sample was obtained by summing the 14-day totals for all subjects. Using 4 as the maximum daily score, the maximum score per evaluation for 25 subjects would be 100 and the maximum grand total for 6 evaluations would be 600. Thus, if the grand total scores are used, the minimum would be 0 with a maximum of 600.

In this test, three dose levels of glycolic acid (0%, 5% and 10%) were formulated with three doses of retinol )0.00%, 0.15% and 0.30%) to produce nine test compositions. The test compositions contained the formulation set forth in Table III, and the varying amounts of glycolic acid and retinol were added, with water to make up the remainder of the formulation. Thus, the nine test compositions contained, respectively, 0% glycolic acid and 0% retinol, 0% glycolic acid and 0.15% retinol, 0% glycolic acid and 0.30% retinol, 5% glycolic acid and 0% retinol, 5% glycolic acid and 0.15% retinol, 5% glycolic acid and 0.30% retinol, 10% glycolic acid and 0% retinol, 10% glycolic acid and 0.15% retinol, and 10% glycolic acid and 0.30% retinol. The test compositions were tested on 29 human subjects using the foregoing protocol to measure skin irritation. Two of the subjects were excluded from analysis because they dropped out of the study. The results of the cumulative irritation study were calculated by summing the six daily irritation ratings made over the 14-day study period for each subject. Twenty-seven subjects were tested. The maximum score on any day for any subject was 4, therefore the maximum possible index was 648 (27×4×6). The results of the study were as follows:

| | Cumulative Irritation Indices Retinol | | |
|---|---|---|---|
| Glycolic Acid | 0.00% | 0.15% | 0.30% |
| 0% | 8.0 | 46.0 | 54.0 |
| 5% | 7.0 | 28.0 | 47.5 |
| 10% | 8.0 | 23.5 | 49.5 |

From these results it can be seen that glycolic acid, when tested without retinol, produced only minimal irritation that was approximately equivalent to the base formulation without glycolic acid or retinol. When retinol was tested alone, without glycolic acid, both doses (0.15% and 0.30%) produced more irritation than the base formulation. The irritative effects of 0.15% and 0.30% retinol were about equivalent. The test demonstrates that, at levels of 0.15% retinol, the addition of glycolic acid provided ameliorative effects: at a level of 5% glycolic acid, irritation was reduced by about 40%; at a level of 10% glycolic acid, irritation was reduced by about 50%. The cumulative irritation of 0.30% retinol compositions was essentially unchanged by the presence of glycolic acid.

Thus, a preferred range of amounts of glycolic acid effective to ameliorate irritation at a retinol level of about 0.01 to about 0.15% is between about 0.01 and about 10% by weight of the composition.

The glycolic acid at the preferred pH range may be present in the formulation as a free acid or in the form of a salt. It may be in the form of inorganic alkali salts such as sodium glycolate or may be in the form of an organic salt such as an amine salt.

TABLE III

| Ingredient | % w/w |
|---|---|
| Light Mineral Oil NF | 25.00 |
| Hydroxyoctacosanyl Hydroxystearate (Elfacos 26) | 6.00 |
| Sorbitol Solution | 5.00 |
| Methoxy PEG-22/Dodecyl Glycol Copolymer (Elfacos E200) | 5.00 |
| PEG-45/Dodecyl Glycol Copolymer (Elfacos ST9) | 3.00 |
| Stearoxytrimethylsilane | 1.00 |
| Dimethicone (50 cstk) | 1.00 |
| Methylparaben, NF | 0.30 |
| Propylparaben, NF | 0.20 |
| Chemoderm 6401/B | 0.15 |
| Quaternium 15 (Dowicil 200) | 0.10 |
| Edetate Disodium, USP | 0.10 |
| Ascorbic Acid | 0.10 |
| Butylated Hydroxytoluene, NF | 0.05 |
| 50% Aqueous NaOH | Q.S. pH 4.7 |
| Purified Water, USP | Q.S. 100% |

What is claimed is:

1. In a skin care composition comprising retinol as an active ingredient, the improvement wherein the retinol irritating properties of the composition are ameliorated by employing retinol irritation ameliorating amounts of glycolic acid.

2. The composition of claim 1 wherein said retinol ameliorating amounts is effective to ameliorate the irritating properties of the composition as evidenced by transepidermal water loss and skin fold thickness measurements.

3. The composition of claim 1 wherein said glycolic acid is present in an amount of at least about 2% by weight of the composition.

4. A composition of claim 3 wherein said glycolic acid is present in a concentration of about 5 to about 10% by weight of said composition.

5. The composition of claim 1 wherein said retinol is present in a quantity of about 0.001 to 5% by weight of the composition.

6. The composition of claim 1 wherein the oil phase of said composition is in weight ratio to the water phase in a ratio from about 5:95 to about 99:1.

7. The composition of claim 6 wherein said composition further comprises a chemical stabilizing system selected from the group consisting of:
   a) a chelating agent and at least one oil soluble antioxidant;
   b) a chelating agent and at least one water soluble antioxidant; and
   c) antioxidant present in each of the oil and water phases of said composition.

8. A method of ameliorating the retinol irritating properties of a composition containing retinol comprising topically administering a retinol irritation ameliorating amount of glycolic acid.

9. The method of claim 8 wherein said glycolic acid is administered in a composition comprising at least about 2% glycolic acid.

10. The method of claim 9 wherein said glycolic acid is administered in a composition comprising about 5% to about 10% glycolic acid.

11. In a skin care composition comprising retinol as an active ingredient, the improvement wherein the retinol irritating properties of the composition are ameliorated by employing a composition consisting essentially of retinol irritation ameliorating amounts of glycolic acid.

* * * * *